United States Patent
Teitelbaum

Patent Number: 5,332,402
Date of Patent: Jul. 26, 1994

[54] PERCUTANEOUSLY-INSERTED CARDIAC VALVE

[76] Inventor: George P. Teitelbaum, 12138 Laurel Terrace Dr., Studio City, Calif. 92604

[21] Appl. No.: 881,969
[22] Filed: May 12, 1992
[51] Int. Cl.⁵ ............................................. A61F 2/24
[52] U.S. Cl. ............................................. 623/2; 623/900
[58] Field of Search ................................. 623/2, 900

[56] References Cited

U.S. PATENT DOCUMENTS

| | | | |
|---|---|---|---|
| 3,626,518 | 12/1971 | Leibinsohn | 623/2 |
| 3,691,567 | 9/1972 | Cromie | 623/2 |
| 3,868,956 | 3/1975 | Alfidi et al. | 606/194 |
| 3,911,502 | 10/1975 | Boretos | 623/2 |
| 4,030,142 | 6/1977 | Wolfe | 623/2 |
| 4,503,569 | 3/1985 | Dotter | 604/8 X |
| 4,759,758 | 7/1988 | Gabbay | 623/2 |
| 4,994,077 | 2/1991 | Dobben | 623/2 |

*Primary Examiner*—Randall L. Green
*Assistant Examiner*—Mary Beth Jones
*Attorney, Agent, or Firm*—James H. Laughlin, Jr.

[57] ABSTRACT

A cardiac valve implanted within the heart is given where a expansible valve maintained in a collapsed form by cold temperature is percutaneously inserted along a releasable guide wire in a cooled sheath and when positioned is expanded by withdrawing the cold temperature.

8 Claims, 2 Drawing Sheets

PERCUTANEOUSLY-INSERTED CARDIAC VALVE

BACKGROUND OF THE INVENTION

1. FIELD OF THE INVENTION

This invention relates to cardiac valvular surgery techniques for replacement of diseased cardiac valves. More particularly, this invention relates to materials and techniques for replacement of diseased mitral valves in humans as well as other animals.

2. PRIOR ART

Cardiac valvular surgery is performed in cases where there is a diminished flow area within a cardiac valve which results in a blockage of normal flow. This blockage leads to cardiac failure. Cardiac valvular surgery may also be required in cases of valvular incompetence in which back flow of blood occurs across a valve that cannot close fully. This is also known as valvular regurgitation Each of the above conditions are frequently due to rheumatic heart disease. Replacement of stenotic or narrowed cardiac valves and regurgitant or incompetent cardiac valves requires open-heart surgery which utilizes a heart-lung machine.

Expansible devices for implantation have been known by the medical community. These devices include, for example, the so-called recovery metals such as titanium-nickel equiatomic intermetallic compounds which demonstrate mechanical "memory" whereby after being formed into specific shapes, these metals are compressed or otherwise given temporary different shapes for insertion and thereafter, when in place, are expanded whereby their mechanical "memory" of the originally formed shape causes the device to assume its originally formed shape.

Materials which are known for having properties useful in such systems include nickel based alloys such as those described in U.S. Pat. No. 3,174,851. Typically, these materials comprise 52 to 56 percent nickel by weight with the remainder being titanium. An initial shape may be permanently set into such recovery metals by heating them while they are held in the desired configuration. The forming temperature for setting the initial shape into the described titanium-nickel alloy is typically about 930° F. The alloy is then cooled and thereafter deformed plastically to a deformed configuration which can be retained until the alloy is reheated to a transition temperature whereafter the alloy will recover its initial configuration.

Various implantable appliances have been described in the patent literature. For example, U.S. Pat. No. 3,868,956 uses an expansible appliance implanted with a vessel through a catheter involving a positioning device. The positioning device is complex because it requires the use of electrical conductors to heat the expansible appliance to allow it to function. U.S. Pat. No. 4,503,569 positions and expands a graft prosthesis using hot saline.

Generally, the known art applies these techniques to the repair of blood vessels narrowed or occluded by disease.

If a satisfactory means could be devised of replacing diseased cardiac valves percutaneously, many major open-heart surgeries could be avoided.

SUMMARY OF THE INVENTION

This invention generally describes a device that serves as a replacement for a diseased (either stenotic or regurgitant) cardiac valve. The device is inserted percutaneously via an appropriately sized small sheath, such as, for example, a 14F sheath using the jugular venous routes. The sheath is positioned to extend across the interatrial septum.

The device is fabricated from a "shaped memory" alloy, nitinol, which is composed of nickel and titanium. Nitinol wire is first fashioned into the desired shape for the device and then the device is heat annealed. When the components of the valve are then exposed to ice-cold temperatures, they become very flexible and supple, allowing them to be compressed down and pass easily through the delivery sheath. A cold temperature is maintained within the sheath during delivery to the deployment site by constantly infusing the sheath with an iced saline solution. Once the valve components are exposed to body temperature at the end of the sheath, they instantaneously reassume their predetermined shapes, thus allowing them to function as designed.

The percutaneous cardiac valve has two possible designs, each of which consists of two components. In the first design, one of the components is a meshwork of nitinol wire of approximately 0.008 inch gauge formed into a tubular structure with a minimum central diameter of 20 min. Away from its central portion, the tubular structure flares markedly at both ends in a trumpet-like configuration. The maximum longitudinal dimension of this component which shall be referred to as the stent or doubly-flared stent is approximately 20 mm. The maximum diameter of the flared ends of the stent is approximately 30 mm. The purpose of the stent is to maintain a semi-rigid patent channel through the diseased cardiac valve following its balloon dilation. The flared ends of the stent maintain the position of this component across the native valve following deployment. The stent contains a thin hydrophilic plastic coating that helps prevent thrombus formation along the inner surface of the stent.

In the second component of the first percutaneous cardiac valve design is referred to as the sliding obturator. At one end of this component are two nitinol wires of 0.038 inch diameter which are fashioned into dual loops a right angles to one another. At the other end these dual wires are connected to an umbrella-shaped structure composed of small, thin slats of nitinol metal covered by silicone rubber with a hydrophilic coating. The dual wires and umbrella structure can be compressed down so as to fit through a 14F delivery sheath with continuous flushing of this sheath with ice-cold heparinized saline. When exposed to body temperature at the end of the delivery sheath, the sliding obturator will expand to its functional size, with a final umbrella diameter of 20-25 mm.

The sliding obturator will be deployed within the expanded stent. The loop formed by the dual wires of the sliding obturator will have sufficient diameter so as not to allow the sliding obturator being carried away by the force of blood flow. The umbrella portion of the sliding obturator will flair out so that its widest diameter will face the interior of the cardiac ventricle. This will allow the sliding obturator to move forward during diastole (relaxation of the heart), thus opening the valve and allowing filling of the ventricle. However, during systole (contraction of the heart), when there is markedly increased intraventricular pressure, the force of blood will act against the open or widest portion of the umbrella pushing back against the flared opening of the wire mesh stent, thus closing the valve. The sliding obturator will therefore allow blood flow in only one direction.

The second version of the percutaneous cardiac valve is the ball design. In this design, the distal end of the wire mesh stent possesses two curved wires that extend beyond the stent into the ventricle, forming a cage structure that will house a small silicone rubber sphere or ball. The silicone sphere will have a hydrophilic coating to diminish thrombogenicity. The silicone sphere will be introduced deflated attached to the end of an 8F catheter through the same delivery sheath used for the placement of the stent with the distal cage. Once in position within the cage, the sphere will be inflated with a polymer mixture that will have a rapid set-up time (it will harden within minutes). After the sphere has been inflated it will be separated from its delivery catheter and will remain inflated due to a self-sealing valve at its attachment point with the delivery catheter. During diastole (ventricular falling stage), the sphere will be carried forward by blood flow, thus opening the valve. The cage will act to restrict the motion of the sphere, preventing it from being lost within the ventricle. During systole, the sphere will be forced backwards due to markedly increased intraventricular pressure, thus closing the valve. The design of the second version of the percutaneous cardiac valve is similar to the Starr-Edwards cardiac valve which also uses a ball-valve mechanism to allow only one-way flow through the valve.

Both versions of the percutaneous cardiac valve are introduced via the right internal jugular venous approach. Following puncture of this vein, a catheter and needle combination are used to puncture the interatrial septum allowing passage of a guide wire and catheter from the right to the left atrium. The same catheter and guide wire or catheter is then floated with blood flow out the left ventricle and into the thoracic aorta. The transjugular guide wire is then captured by a snare or basket and dragged out through the right or left common femoral artery. In so doing, one will have control over both ends of the guide wire used to introduce the percutaneous cardiac valve. Over this guide wire, a high-pressure balloon catheter is advanced across the diseased mitral valve where it is inflated. Once the valve is fully dilated, the balloon catheter is deflated and replaced with a 14F delivery sheath inserted via the right internal jugular approach. The sheath's tip will be positioned in the left ventricle. The nitinol stent (with or without distal cage) is advanced to the site of the dilated valve by means of a pusher rod. All the while, the delivery sheath is being flushed with cold heparinized saline to keep the stent compressed, soft, and flexible. Once the stent has been pushed to the distal end of the sheath where it bridges the site of the dilated valve, the pusher will be held steady while the sheath is withdrawn, allowing the stent to come into contact with body temperature. This will cause the rapid expansion of the stent and create an adequate flow lumen through the diseased valve.

At this point, either the sliding obturator or the silicone sphere are deployed with the appropriate valve stent. Since both versions of the stent have a hydrophilic silicone coating, when the sliding obturator or silicone sphere come into contact with the stent lumen, they seal or close the valve, preventing backflow of blood.

BRIEF DESCRIPTION OF THE DRAWINGS

FIG. 4A shows its position within the stent in systole while FIG. 4B shows its position within the stent in diastole.

DESCRIPTION OF THE PREFERRED EMBODIMENTS

As noted earlier, cardiac valvular surgery is performed in cases where there is a diminished flow area within a cardiac valve which results in a blockage of normal flow which can leads to cardiac failure. Surgery is often required in cases of valvular incompetence in which back flow of blood occurs across a valve that cannot close fully. Replacement of stenotic and regurgitant cardiac valves can be accomplished in accordance with this invention using percutaneous techniques allowing for avoidance of many major open-heart surgery procedures.

This invention describes a device that serves as a replacement for a diseased stenotic or regurgitant cardiac valve. By this invention, a technique and the devices which serve as a replacement for a stenotic or regurgitant diseased cardiac valves is given. This technique and the devices employed are particularly useful in replacement of diseased mitral valves.

In this invention, compressed devices are inserted percutaneously by way of an appropriately sized sheath using the jugular venous routes and expanded to form new valve mechanisms which provide replacement cardiac valves.

The catheter and delivery sheath of this invention are appropriately sized for use. One such appropriate catheter is a 14F plastic catheter used for delivery and deployment of both stents and the valve structures of this invention. Such a delivery sheath is used in the normal matter and may have a pusher capable of moving a stent or other valve part to its ultimate location in the heart.

Figure 1:
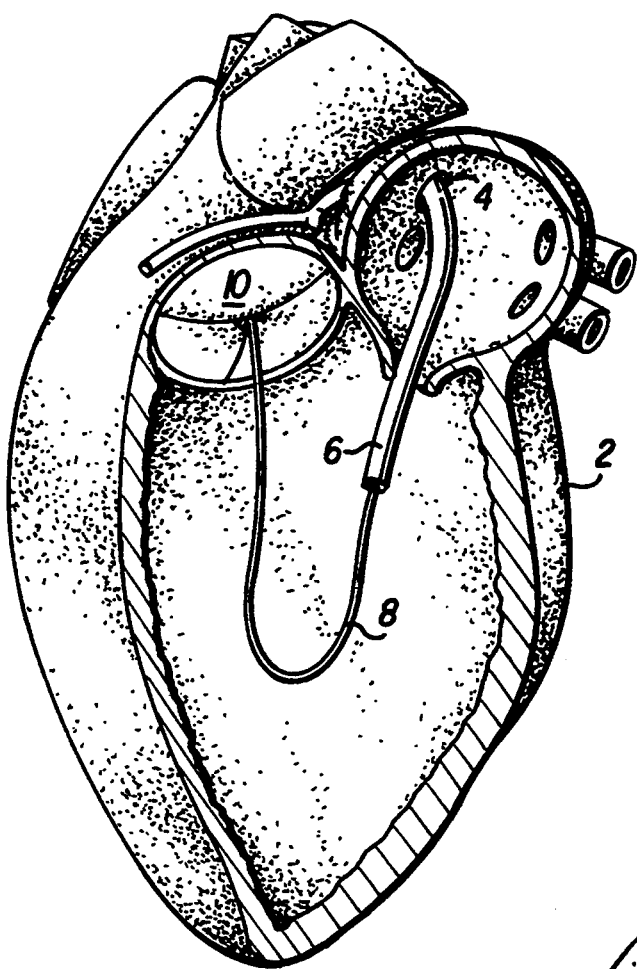
FIG. 1 is a cutaway portion of a heart showing the catheter following a guide wire entering through the interatrial septum.
Figure 2:
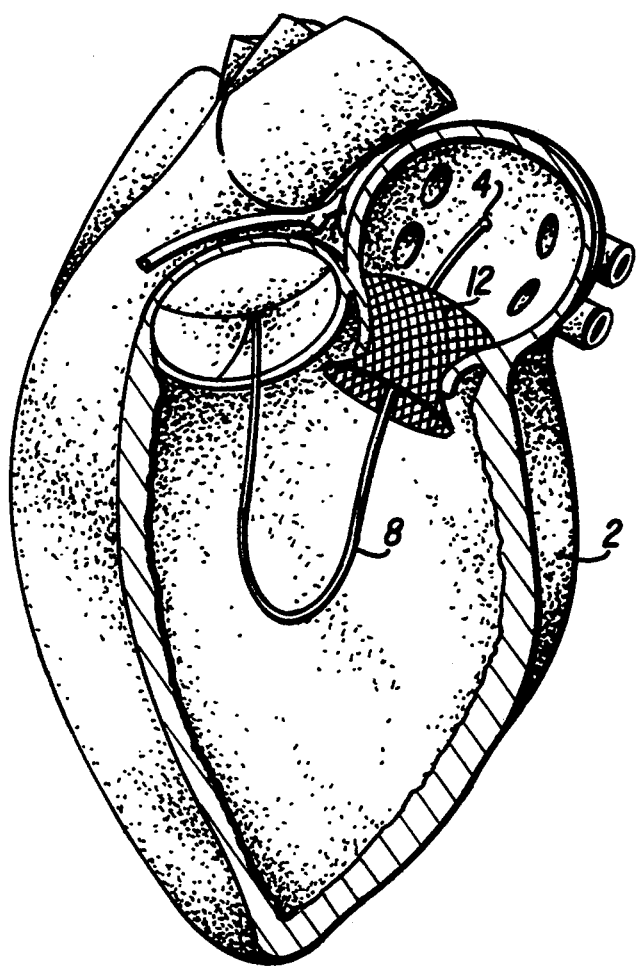
FIG. 2 is a cutaway portion of a heart showing the stent in place along the guide wire after the catheter has been withdrawn from the heart.
Figure 3:
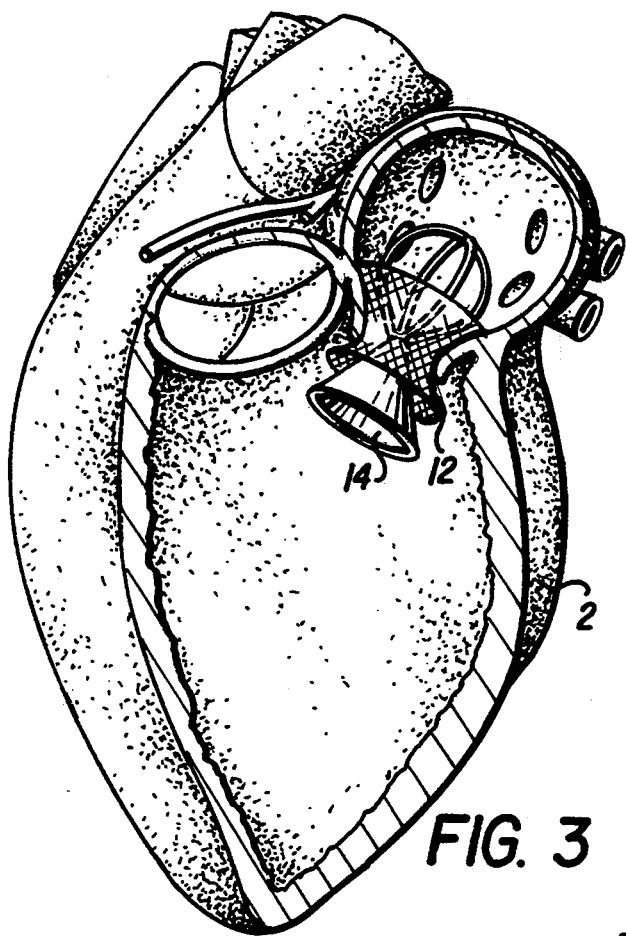
FIG. 3 is a cutaway portion of a heart showing the installed cardiac valve, a sliding obturator, positioned within the stent.

With reference to FIG. 1, FIG. 2 and FIG. 3, in the technique and procedure of this invention, the percutaneous cardiac valve is introduced via the right internal jugular venous approach. Following puncture of this vein, a catheter and needle combination (not shown) are used to puncture the interatrial septum 4 allowing passage of a guide wire 8 and catheter 6 from the right to the left atrium. The same catheter and guide wire or catheter is then floated with blood flow out the left ventricle and into the thoracic aorta 10. The transjugular guide wire is then captured by a snare or basket (not shown) and dragged out through the right or left common femoral artery. This allows control over both ends of the guide wire used to introduce the percutaneous cardiac valve.

Over the guide wire 8, a high-pressure balloon catheter (not shown) is advanced across the diseased mitral valve where it is inflated. Once the valve is fully dilated, the balloon catheter is deflated and replaced with a 14F delivery sheath 6 inserted via the right internal jugular approach. The sheath's tip will be positioned in the left ventricle. A compressed nitinol stent, doubly-flared stent 12 as shown, is advanced to the site of the dilated valve by means of pusher rod (not shown). All the while, the delivery sheath is being flushed with iced cold heparinized saline to keep the stent compressed, soft, and flexible. Once the stent has been pushed to the distal end of the sheath 6 where it bridges the site of the dilated valve, the pusher will be held steady while the sheath is withdrawn allowing the stent to come into contact with body temperature. This will cause the rapid expansion of the stent 12 as shown in FIG. 2 and create a channel for adequate flow lumen through the diseased valve.

At this point, a valve mechanism is inserted. While various valve mechanisms can be employed, this invention is particularly effective with a sliding obturator 14 position as shown in FIG. 3 and shown in more detail in FIG. 4. Alternatively, a silicone sphere can be deployed with the appropriate valve stent as shown in FIG. 5. Since both versions of the stent have a hydrophilic silicone coating, when the sliding obturator or silicone sphere come into contact with the stent lumen, a seal is created when the valve is closed preventing backflow of blood.

The devices of this invention are fabricated from a "shaped memory" alloy, nitinol, which is composed of nickel and titanium. Nitinol wire is first fashioned into the desired shape for the device and then the device is heat annealed. When the components of the valve are then exposed to ice-cold temperatures, they become very flexible and supple, allowing them to be compressed down and pass easily through a delivery sheath. Cold temperature is maintained with the sheath during delivery to the deployment site by constantly infusing the sheath with an iced saline solution. Once the valve components are exposed to body temperature at the end of the sheath, they instantaneously reassume their predetermined shapes, thus allowing them to function as designed.

The sliding obturator cardiac valve has two components. As shown in FIG. 2, one of the components is a stent 12 which comprises a meshwork of nitinol wire of approximately 0.008 inch gauge formed into a tubular structure with a minimum central diameter of 20 mm. Away from its central portion, the tubular structure flares markedly at both ends in a trumpet-like configuration. The maximum longitudinal dimension of this stent, or more particularly, a doubly-flared stent, is approximately 20 mm. The maximum diameter of the flared ends of the stent is approximately 30 mm. The purpose of the stent is to maintain a semi-rigid patent channel through the diseased cardiac valve following its balloon dilation as shown in FIG. 2. The flared ends of the stent maintain the position of this component across the native valve following deployment. The stent contains a thin hydrophilic plastic coating (not shown) that helps prevent thrombus formation along the inner surface of the stent.

Figure 4:
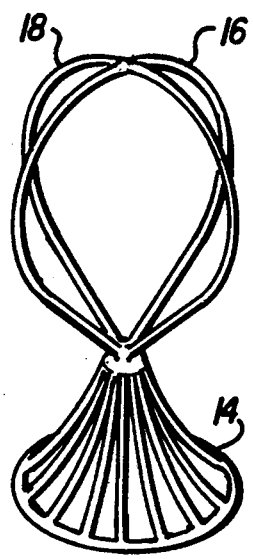
FIG. 4 is a perspective view of the sliding obturator of this invention in its expanded and normal form.
Figure 5:
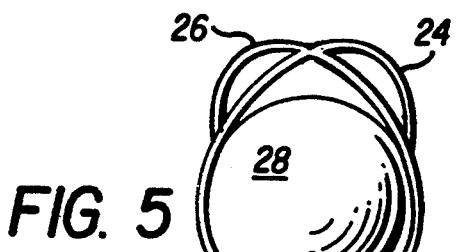
FIG. 5 is a perspective view of a different embodiment of this invention, namely, a ball valve and stent design.

The second component of the sliding obturator valve design is shown in FIG. 4. At one end of this component are two nitinol wires of 0.038 inch diameter which are fashioned into dual loops 16 and 18 at right angles to one another. At the other end these dual wires are connected to an umbrella-shaped structure 20 composed of small, thin slats of nitinol metal covered by silicone rubber with a hydrophilic coating. The dual wires and umbrella structure can be compressed down so as to fit through a delivery sheath with continuous flushing of this sheath with ice-cold heparinized saline. When exposed to body temperature at the end of the delivery sheath, the sliding obturator will expand to its functional size, with a final umbrella diameter of 20-25 mm.

Figure 4A:
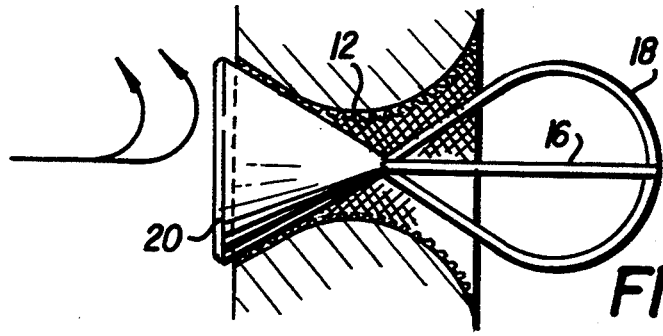
FIG. 4A is and FIG. 4B are partial side views of the sliding obturator of FIG. 4 inserted and in use where
Figure 4B:
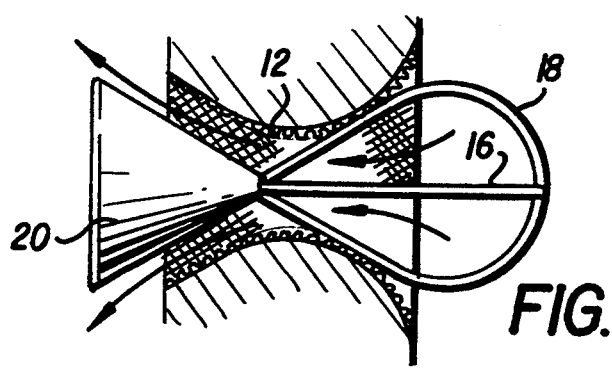

The sliding obturator will be deployed within the expanded stent as shown in FIG. 4A and 4B. The loops 16 and 18 formed by the dual wires of the sliding obturator will have sufficient diameter so as not to allow the sliding obturator being carried away by the force of blood flow. The umbrella portion 20 of the sliding obturator will flair out so that its widest diameter will face the interior of the cardiac ventricle. This will allow the sliding obturator to move forward during diastole or relaxation of the heart as shown in FIG. 4B, thus opening the valve and allowing filling of the ventricle allowing flow as shown by arrows. However, during systole or contraction of the heart, when there is markedly increased intraventricular pressure, the force of blood will act against the open or widest portion of the umbrella 20 as shown in FIG. 4A pushing back against the flared opening of the wire mesh stent, thus closing the valve. The sliding obturator will therefore allow blood flow in only one direction.

Figure 6:
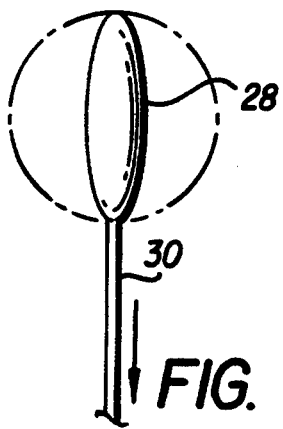
FIG. 6. is a view of the ball of the ball valve of FIG. 5 after inflation.

In another embodiment of the percutaneous cardiac valve which may be used in this invention, a ball design is employed. In this design as shown in FIG. 5, the distal end of the wire mesh stent possesses two curved wires 24 and 26 that extend beyond the stent into the ventricle, forming a cage structure that will house a small silicone rubber sphere or ball 28. The silicone sphere will have a hydrophilic coating to diminish thrombogenicity. The silicone sphere will be introduced deflated (not shown) attached to the end of a smaller catheter, such as, for example one sized 8F, through the same delivery sheath used for the placement of the stent with the distal cage. Once in position within the cage, the sphere will be inflated with a polymer mixture that will have a rapid set-up time hardening within minutes. Silicone materials are well known to be suitable for this purpose. After the sphere has been inflated as shown in FIG. 6, it will be separated from its delivery catheter and will remain inflated due to a self-sealing valve 30 at its attachment point with the delivery catheter. During diastole or the ventricular filling stage, the sphere will be carried forward by blood flow, thus opening the valve. The cage will act to restrict the motion of the sphere, preventing it from being lost within the ventricle. During systole, the sphere will be forced backwards due to markedly increased intraventricular pressure, thus closing the valve. The design of the ball version of the percutaneous cardiac valve useful in this invention is similar to the Starr-Edwards cardiac valve which also uses a ball-valve mechanism to allow only one-way flow through the valve.

Uniquely in this invention, the stent and valves of this invention are made from a shaped memory nitinol alloy with a transition temperature in the range of about 90° to about 96° F. and preferably about 95° F. Those skilled in the art will appreciate that the transition temperatures of the nitinol family of alloys can be manipulated over a wide range by altering the nickel-titanium ratio, by adding small amounts of other elements, and by varying deformation and annealing processes. Therefore, no further description of the composition of the shape memory nitinol alloy is necessary.

In this invention, the cool and cold temperatures used are those temperatures below about 75° F. In particular, iced-cold temperatures are generally below about 32° F. and those skilled in the art will appreciate that the compression temperatures of the nitinol family of alloys can be manipulated over a wide range by altering the nickel-titanium ratio, by adding small amounts of other elements, and by varying deformation and annealing processes. Therefore, no further description of the composition of the shape memory nitinol alloy is necessary.

While this invention has been described in its preferred form with a certain degree of particularity, it is understood that the present disclosure of the preferred forms and embodiments have been made only by way of example and that numerous changes in the details of construction and the combinations and arrangement of parts may be resorted to without departing from the spirit and the scope of the invention as claimed.

What is claimed is:

1. A method of implanting an expansible cardiac valve within a heart wherein the expansible cardiac valve is comprised of a recovery metal having memory and which is capable of expanding to a desired shape comprising:

releasably coupling a cardiac valve in a compressed form to a positioning device while maintaining a cool temperature sufficient to maintain the cardiac valve in said compressed form and which is capable of passing through heart within which the cardiac valve is to be implanted;

manipulating the positioning device within the heart so as to position the cardiac valve at a desired location with the heart;

ceasing maintaining cool temperature to effect expansion of the cardiac valve to a desired shape wherein the valve engages the walls of the heart;

disengaging the positioning device from the expanded cardiac valve; and removing the positioning device to leave the cardiac valve implanted within the heart.

2. The method of claim 1 wherein the cardiac valve comprises a stent and sliding obturator.

3. The method of claim 1 wherein the cardiac valve comprises stent and caged ball.

4. The method of claim 1 wherein the cardiac valve expands at about body temperature.

5. The method of claim 1 wherein the cardiac valve is a mitral valve.

6. A cardiac heart valve comprising a stent and sliding obturator formed of a shaped memory alloy which has a transition temperature of from about 90° to about 96° F.

7. The cardiac heart valve of claim 6 wherein the transition temperature is about 95° F.

8. A mitral cardiac heart valve comprising a stent and ball and cage formed of a shaped memory alloy which has a transition temperature of from about 90° to about 96° F.

* * * * *